United States Patent [19]

Schnell et al.

[11] Patent Number: 4,620,284

[45] Date of Patent: Oct. 28, 1986

[54] QUALITATIVE AND QUANTITATIVE ANALYSIS USING RAMAN SCATTERING

[75] Inventors: Robert P. Schnell, Deerfield; Robert W. Sampson, Wayne; Ronald F. Pacanowski, Hoffman Estates; Donald J. Bruggema, Wheeling, all of Ill.

[73] Assignee: UOP Inc., Des Plaines, Ill.

[21] Appl. No.: 566,842

[22] Filed: Dec. 29, 1983

[51] Int. Cl.$^4$ .......................... G06F 15/20; G01J 3/44
[52] U.S. Cl. ...................................... 364/498; 356/301
[58] Field of Search ................ 364/496–499, 364/525; 356/301, 306, 307

[56] References Cited

U.S. PATENT DOCUMENTS

| | | | |
|---|---|---|---|
| 2,527,121 | 10/1950 | Dudenbostel | 356/301 |
| 2,527,122 | 10/1950 | Heigl et al. | 356/301 |
| 2,940,355 | 6/1960 | Cary | 356/301 |
| 3,414,354 | 12/1968 | Siegler | 356/301 |
| 3,556,659 | 1/1971 | Hawes | 356/301 |
| 3,625,613 | 12/1971 | Abell et al. | 356/301 |
| 3,723,007 | 3/1973 | Leonard | 356/301 |
| 3,820,897 | 6/1974 | Roess | 356/301 |
| 4,030,827 | 6/1977 | Delhaye et al. | 356/301 |
| 4,068,953 | 1/1978 | Harney et al. | 356/301 |
| 4,127,329 | 11/1978 | Chang et al. | 356/301 |
| 4,195,930 | 4/1980 | Delhaye et al. | 356/301 |
| 4,267,572 | 5/1981 | Witte | 364/498 |
| 4,270,864 | 6/1981 | Barrett et al. | 356/301 |
| 4,365,303 | 12/1982 | Hannah et al. | 364/498 |
| 4,397,556 | 8/1983 | Müller | 356/301 |
| 4,505,586 | 3/1985 | Tochigi et al. | 356/301 |

OTHER PUBLICATIONS

Analytical Chemistry, vol. 21, No. 5, May 1949, pp. 554–559, "Determination of Total Olefins and Total Aromatics", by J. J. Heigl et al.

Proceedings of the American Petroleum Institute, vol. 27–28, 1948, pp. 95–105, "Determination of Total Olefins and Total Aromatics", by J. J. Heigl et al.

Report of a Conference held by The Institute of Petroleum in London on Oct. 28–29, 1954 entitled "Molecular Spectroscopy".

*Primary Examiner*—Gary Chin
*Attorney, Agent, or Firm*—Thomas K. McBride; John F. Spears, Jr.; Richard J. Cordovano

[57] ABSTRACT

Methods and apparatus are provided for qualitative and quantitative analysis utilizing the Raman effect. Analyses are obtainable without exercise of human judgment or human interpretation. Analyses may be obtained on-line in the field or in a laboratory. A wide range of fluids and solids are capable of rapid routine analysis without major adjustment of equipment. An analysis is obtained by comparing a Raman spectrum of the unknown sample to Raman spectra of samples whose analysis is known. The known Raman spectra are stored in computing means in digital form and the comparison is accomplished by the computing means.

32 Claims, 4 Drawing Figures

QUALITATIVE AND QUANTITATIVE ANALYSIS USING RAMAN SCATTERING

BACKGROUND OF THE INVENTION

This invention relates to the detection of substances and measurement of the quantities present. More particularly, it relates to qualitative and quantitative analysis utilizing Raman spectra of the substances under analysis.

The Raman effect, or Raman scattering, is well known. Briefly and simply, when a beam of light impinges on substances, light is scattered. This scattering is of several different types, the predominant type being Rayleigh scattering, wherein the wave length of the scattered light is the same as that of the incident light. In the type utilized in the present invention, Raman scattering, the scattered light is of different wave lengths than the incident light; photons are absorbed by the substance and re-emitted at higher and lower wave lengths. A Raman spectrum of a substance is constituted of Raman scattered light and is spread across a wave length band even if the incident light is monochromatic, that is, all of a single wave length. There is a separate Raman spectrum of a particular substance for, or associated with, each incident wave length. In practice, a monochromatic beam of incident light is always used in Raman spectroscopy because of the difficulties in obtaining spectral separation. When Raman and Rayleigh scattered light is resolved into a spectrum by a spectrograph, Raman lines will appear on both sides of the Rayleigh line. The Raman line or lines on the low frequency side (or low wave number side or high wave length side) of the Rayleigh line are more intense than those on the high frequency side and are called the Stokes line or lines; those on the high frequency side are called the anti-Stokes line or lines. Not all substances are Raman active; there must be a change in polarizability during molecular vibration in order that a substance be Raman active. Substances which do exhibit Raman spectra can be characterized by means of their spectra. Qualitative analysis of a substance can be accomplished by comparison of the locations of its Raman lines with those of known standards. Quantitative analysis can be accomplished by comparison of intensities of Raman lines; this is generally a linear relationship. Of course, spectra which are compared must result from exciting radiation of the same wave length. For purposes of this document, a substance is defined as any composition of matter, including a single element and a mixture or solution of chemical compounds.

Raman spectroscopy has numerous applications and is a major research tool. It is now a rapidly developing area, having been neglected for many years in favor of infrared spectroscopy and ultraviolet spectroscopy. Advances in the equipment available for Raman spectroscopy, particularly the development of lasers as a source of monochromatic light, have provided much impetus. A review of the field of Raman spectroscopy, including theory, applications, potential, and citations to additional literature is provided by two recent publications: *Raman Spectroscopy*, Long, McGraw-Hill, 1977 and *Chemical Applications of Raman Spectroscopy*, Grasselli et al., Wiley and Sons, 1981.

Though Raman spectroscopy is an important research technique and is used for qualitative and quantitative analysis, there has not been available a Raman analyzer, that is, apparatus which provides, rather than a spectrum, an output comprising indication of substances present in a sample and, in the case of a quantitative analyzer, numbers denoting the amounts present of the constituent substances of a sample. There has not been available a routine method of analysis utilizing the Raman effect which provides qualitative or quantitative results which need no further processing or interpretation. Further lacking has been universal Raman effect apparatus and methods; that is, those that can be used for a wide variety of samples without significant change to the apparatus being required when different substances are to be analyzed. There are significant advantages in effecting qualitative and/or quantitative analysis using Raman spectroscopy in place of or in addition to conventional analysis methods.

INFORMATION DISCLOSURE

U.S. Pat. No. 4,068,953 (Harney et al.) deals with methods and apparatus for measuring isotope ratios and isotopic abundances using the Raman effect. Apparatus for remote sensing of gaseous materials is described in U.S. Pat. Nos. 3,820,897 (Roess) and 3,625,613 (Abell) and an improvement to the latter patent is disclosed in U.S. Pat. No. 3,723,007 (Leonard).

U.S. Pat. Nos. 3,414,354 (Siegler) and 3,556,659 (Hawes) describe laser-excited Raman spectrometers. A Raman microprobe for producing micrographic images of certain species in a sample is disclosed in U.S. Pat. No. 4,195,930 (Delhaye et al.). An earlier patent of the same inventors covering similar subject matter is U.S. Pat. No. 4,030,827.

Work accomplished using the Raman effect to analyze hydrocarbons is disclosed in U.S. Pat. Nos. 2,527,121 (Dudenbostel) and 2,527,122 (Heigl et al.) and in an article by Heigl et al. entitled "Determination of Total Olefins and Total Aromatics" which appeared in both *Analytical Chemistry* (Vol. 21, p. 554, 1949) and *Proceedings of the American Petroleum Institute* (Vol. 27–28, p. 90, 1948). Another reference covering the same work is the report of a conference held by The Institute of Petroleum in London in 1954 entitled "Molecular Spectroscopy".

Additional U.S. patents dealing with Raman spectroscopy are 4,127,329 (Chang et al.) and 2,940,355 (Cary). U.S. Pat. No. 4,270,864 (Barrett et al.) is representative of several patents to Barrett dealing with photoacoustical Raman spectroscopy.

U.S. Pat. No. 4,397,556 (Muller) claims method and apparatus for quality control in which the Raman effect is used.

BRIEF SUMMARY OF THE INVENTION

It is an object of this invention to provide methods and apparatus for qualitative and quantitative analysis of substances in gaseous, liquid, or solid form. More specifically, it is an object of this invention to provide the capability of performing analyses rapidly and through a relatively unskilled technician or without a technician in attendance at all. Related is the object of providing methods and apparatus wherein no human judgment and no human interpretation is necessary to produce analyses. It is also an object of this invention to provide methods and apparatus for rapidly analyzing substances which have heretofore required complex procedures involving much sample handling and/or pretreatment by various procedures. Also, it is an object of this invention to provide an analysis which requires only a small amount of sample and to provide a nondestructive method of analysis such that the sample is not altered or consumed. This object is related to that of providing apparatus which consumes little electrical power and does not heat the sample. It is a further object of this invention to provide a method and apparatus to analyze a substance in situ, that is, without withdrawing the substance from a containing vessel or pipeline. It is a still further object of this invention to provide an analysis apparatus which is modular in design and construction, to facilitate troubleshooting and repair. Another object of this invention is to provide a universal method and apparatus instead of such capable of use in analyzing only certain substances or use in only particular specialized applications. It is also desired to provide apparatus which is inexpensive in relation to its utility.

In one of its embodiments, the invention comprises apparatus for performing a quantitative analysis for preselected substances of an unknown sample comprising: (a) means for producing a beam of photons which is substantially monochromatic and impinges on the unknown sample; (b) means for collecting photons scattered by the unknown sample into a stream of scattered photons; (c) means for resolving the photon stream into its component frequencies to form a Raman spectrum of the unknown sample; (d) means for converting said unknown sample Raman spectrum to digital form and transmitting said unknown spectrum to computing means; (e) said computer means, which contain reference spectra obtained in the same manner as said unknown spectrum, where the reference spectra are of reference samples whose quantitative composition is known and where each reference sample is comprised of at least one of said preselected substances; and, (f) means within the computer for identifying substances present in the unknown sample by comparing said unknown spectrum to the reference spectra, said comparison being accomplished by utilizing a method comprising the following steps: (i) inspecting the reference spectra and selecting a plurality of separate spectral analysis regions; (ii) determining the areas of the selected regions for each reference spectrum and for the unknown spectrum; (iii) establishing a relationship between said reference spectra region areas and concentrations of said preselected substances in said reference samples; and (iv) determining the concentrations of said preselected substances in said unknown sample by applying the relationship established in step (f)(iii) to the unknown spectrum region areas.

Said relationship may be established and said concentrations determined by: (a) expressing said reference sample concentrations in terms of concentration fractions and arranging the concentration fractions in a concentration fraction matrix, according to said reference samples and said preselected substances; (b) calculating area fractions from said reference spectra region areas and arranging the area fractions into an area fraction matrix, according to said reference samples and the selected regions; (c) determining a transpose matrix, which is the transpose of the area fraction matrix; (d) forming a mathematical relationship using said matrices, as follows:

$$\frac{\text{concentration fraction matrix} \times \text{tranpose matrix}}{\text{area fraction matrix} \times \text{tranpose matrix}};$$

(e) solving said mathematical quantity to yield a matrix, which consists of correlation coefficients, arranged according to the selected regions and said preselected substances; (f) calculating area fractions from said unknown spectrum region areas and arranging the area fractions in a matrix; and, (g) multiplying said correlation coefficients matrix by the matrix formed of said unknown spectrum area fractions to obtain a product which is a concentration fraction matrix which expresses the concentrations of the preselected substances in said unknown sample.

Composite reference spectra may be used in performing said comparison, a composite reference spectrum being prepared for each reference sample by providing a plurality of spectra of each reference sample to the computer and averaging each of said plurality of reference spectra.

DETAILED DESCRIPTION OF THE INVENTION

In order to aid in gaining an understanding of the invention, the apparatus of a particular embodiment, a hydrocarbon analyzer dedicated to PNA analysis, will be described. The information presented in regard to this embodiment is not meant to limit the scope of the invention in any way. Additional descriptive material applicable to other embodiments is also presented where appropriate. The function of a PNA analyzer is to determine the composition of a hydrocarbon in terms of three hydrocarbon groups, as follows. Paraffins are straight or branched chain hydrocarbons with no double bonds. Naphthenes are ring compounds with no double bonds, and with the ring usually containing 5 or 6 carbon atoms. Aromatics are hydrocarbon compounds that contain at least one 6-carbon ring having three double bonds. The PNA analysis of a hydrocarbon is useful information to oil refinery operators; for example, in a catalytic reforming process, the operating conditions are set by reference to the P, N, and A content of the feed stream to the process. The yield of product from the process is dependent on the operating conditions.

Figure 1:
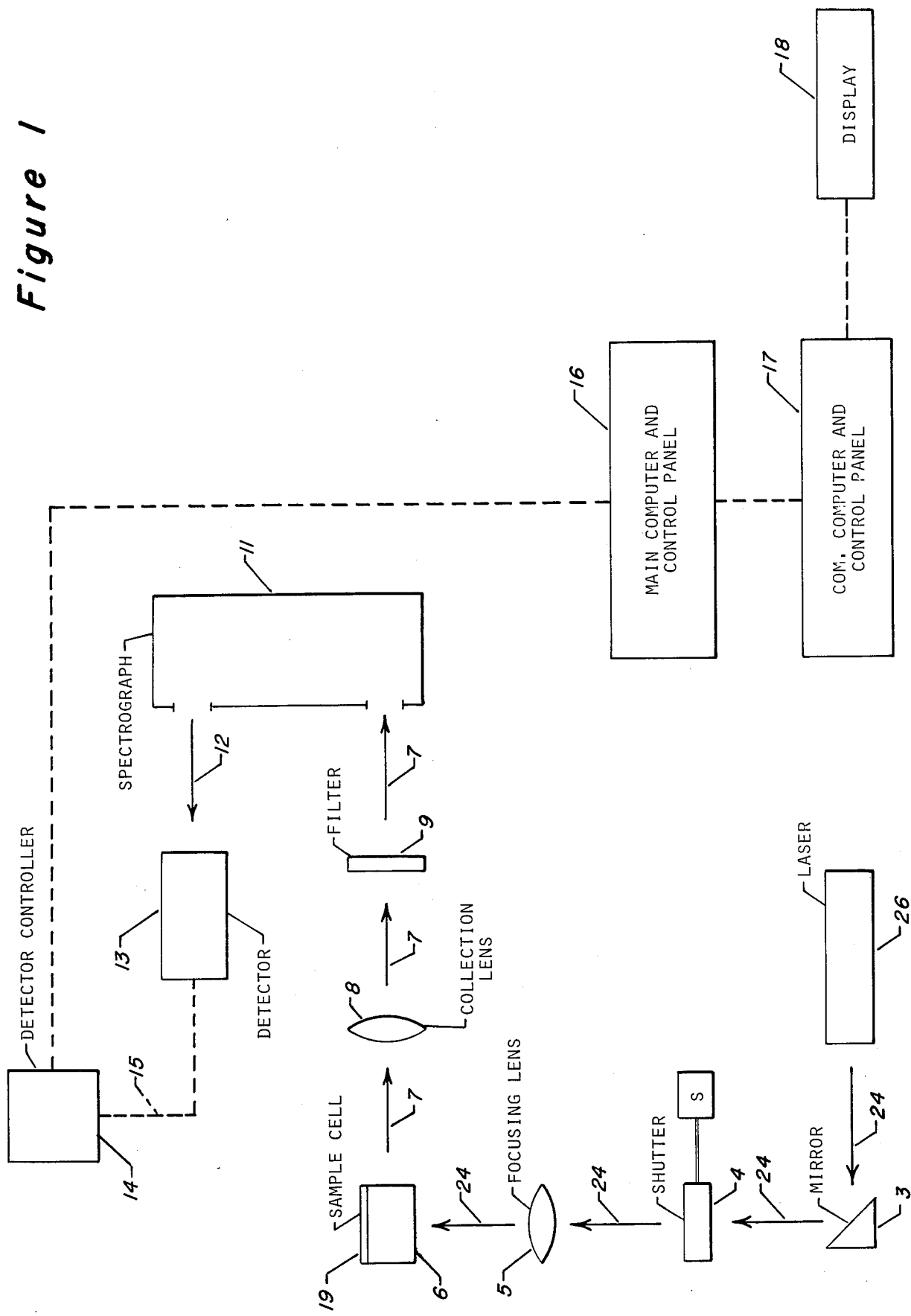
FIG. 1 is a schematic diagram of apparatus used in one embodiment of the invention.

Referring to FIG. 1, laser 26 is the source of monochromatic radiation, or a narrow beam of photons, which serves as the exciting light for the Raman effect. Laser 26 is a 25 milliwatt helium-neon laser, which produces radiation centered about a wave length of 6328 angstroms. Of course, it is not possible to provide totally monochromatic light; the laser light does not form a single line at 6328 angstroms but forms a band centered on that value which has the appearance of a Gaussian curve. However, if the width of the band, or Gaussian curve, is too great, Raman peaks will not be clearly resolved. The band width of the incident light should be almost as narrow as the finest peak which is to be resolved. More precisely, the width of the laser light band at one-half its maximum height should be no more than the width of the narrowest peak to be resolved. Arrows 24 denote the path of the beam of photons produced by laser 26. The direction of the beam of photons is changed by mirror 3, which is a coated dielectric mirror suitable for a helium-neon laser denoted Laser Beam Director by its supplier, Newport Research Corp. The photon beam passes through shutter 4 and focusing lens 5 before impinging on a sample contained in sample cell 6. The function of shutter 4 is to briefly stop the beam of photons from reaching sample cell 6 so that a background spectrum may be obtained, as will be explained herein. Shutter 4, which was supplied by Newport Research Corp., is opened and closed upon signals from main computer 16 by means of wiring which is not shown.

Focusing lens 5 is an achromatic objective of 60 mm focal length supplied by Rolyn Optics Co. Its purpose is to throttle, or concentrate, the beam of photons so that there is a higher photon flux, or energy density impinging on the sample. The diameter of the photon beam before passing through focusing lens 5 is approximately 1.25 mm. The focusing lens is supported in a holder and centering device (not shown) supplied by Ardel-Kinematic of College Point, N.Y. Sample cell 6 is a rectangular block of stainless steel having a cavity bored through it along its longitudinal axis to serve as a sample flow passage. Four quartz optical flats are disposed around the four sides of the block parallel to its longitudinal axis. The optical flats serve as closures (by means of O-rings and appropriate fittings) for cavities in the block which communicate with the sample flow passage. Thus the optical flats form "windows" on the sample stream. The photon beam passes through one window and is reflected back by a coating 19 on the opposite window. The coating consists of aluminum vapor deposited on the outside surface and covered by lacquer for protection of the aluminum. The coating reflects the incident radiation so that it impinges a second time on the sample. Raman scattered light passes through the third window to collection lens 8. The fourth window is provided only for viewing the sample and photon beam. A continuous stream of gaseous or liquid sample flows through sample cell 6 via tubing (not shown) connected to the flow passage. Sample flow may be pictured as being perpendicular to the plane in which FIG. 1 lies. It is not necessary that the sample be flowing through sample cell 6; the substance to be analyzed may be contained in a closed container. A flow-through cell is used in the PNA analyzer, since this embodiment of the invention is adapted for on-line use, or continuous analysis of a flowing stream. There are numerous sample cell designs which are capable of use. For an example, see U.S. Pat. No. 4,410,271 (Matthews). Note that a multi-pass cell design will make available more scattered light, but will also require more precise alignment. It should be noted that substances in solid form may also be analyzed, as will be discussed herein, and do not require containment in a sample cell.

Light scattered by the sample is collected and focused by collection lens 8. The collected scattered light may be referred to as a photon stream. The path of the scattered light used in the apparatus is depicted by arrows 7. Collection lens 8 is a Canon f/1.4 50 mm camera lens. The scattered light is focused on the entrance slit of spectrograph 11 by collection lens 8. The function of collection lens 8 may also be accomplished using more than one lens, a mirror or mirrors, or a combination thereof. Filter 9 is provided in the path of the photon stream to block Rayleigh scattered light and the anti-Stokes portion of the Raman scattered light. It is a sharp cut-off filter supplied by Schott Optical Glass which stops substantially all radiation having a wave length less than 6328 angstroms. It is not necessary to the practice of the invention to prevent light blocked by filter 9 from entering spectrograph 11, but it is common practice to exclude unneeded light to prevent potential problems. An alternative arrangement, should it be desired to include a filter, is to locate it between the spectrograph and detector. Spectrograph 11 resolves light entering it into a spectrum by focusing each component wave length of the entering photon stream at a different horizontal position at the spectrograph exit slit. The spectrum appears as a band of spaced-apart (by wave length) vertical lines of light of varying intensity. The spectrum is commonly visualized as, or converted into, a curve having a series of peaks and valleys, such as the representation of FIG. 4. Spectrograph 11 is denoted as Model No. HR-320 by its supplier, Instruments S.A. Inc. of Metuchen, N.J. The spectrum formed at the exit slit of spectrograph 11 is sensed by detector 13, which converts the spectrum to electrical signals and transmits the signals to detector controller 14. A path from spectrograph 11 to detector 13 is depicted by arrow 12 of the schematic representation. Physically, detector 13 is bolted to spectrograph 11, covering the exit slit.

Figure 2:
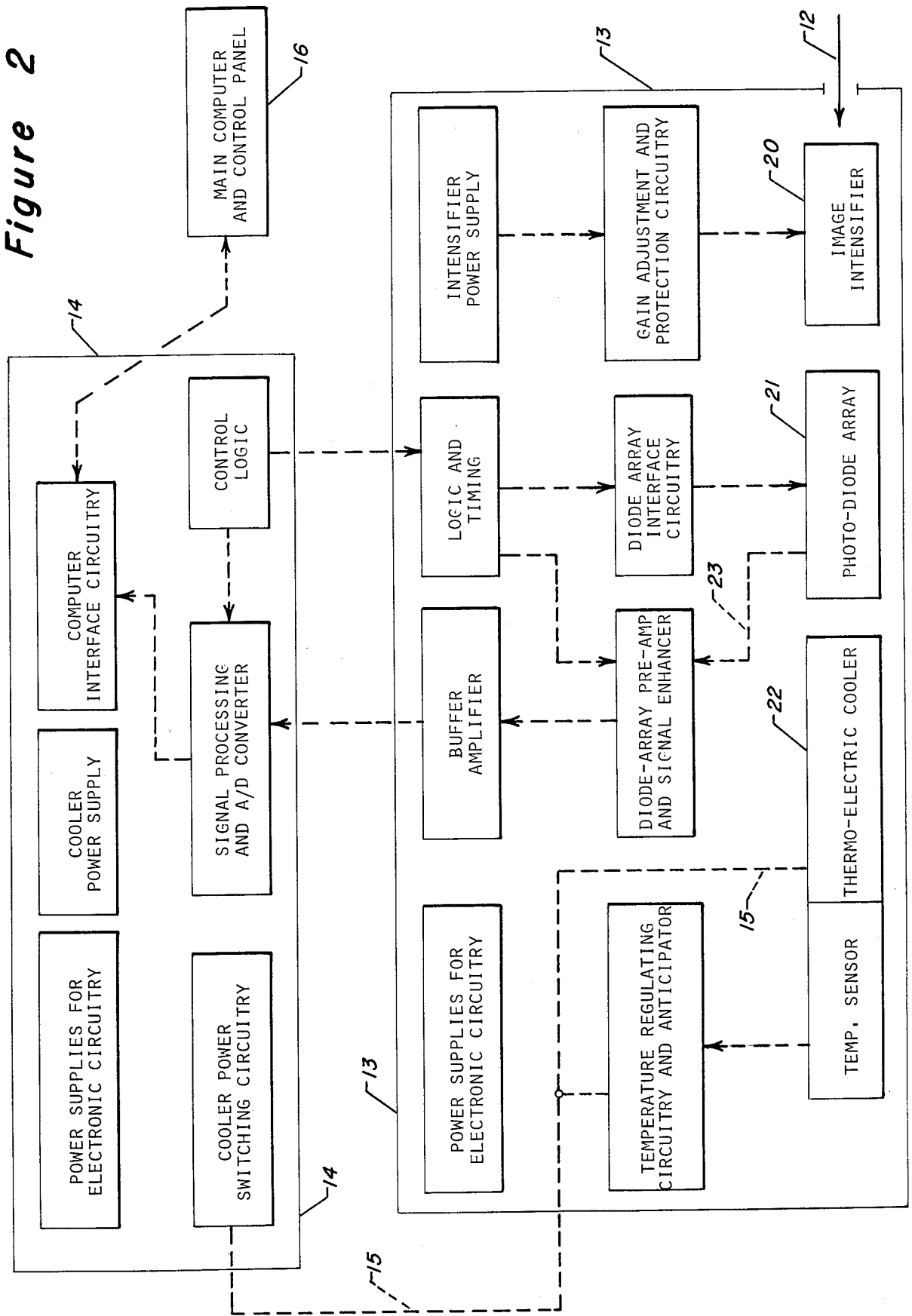
FIG. 2 is a block diagram showing the major components of the detector and detector controller of FIG. 1, which comprise apparatus for converting weak light to electrical signals, in a functional format. Where helpful, signals transmission is depicted.

Information and signal transmittal paths are represented in FIGS. 1 and 2 by means of dashed lines, such as that denoted 15. A dashed line represents a path or paths whose physical form varies according to the type of information and signals, but is usually a wire or wires. Returning to FIG. 1, the signals comprising the spectrum are processed and converted to digital form in detector controller 14 and then transmitted to the main computer, represented by the box denoted 16. Main computer 16 processes the spectrum, as will be described later, and generates a quantitative analysis of the substance flowing through sample cell 6. The analysis is transmitted to communication (com) computer 17, which causes it to appear in human-readable form on display 18, an LED device assembled from commercially available components. Control panels are provided at computers 16 and 17 for human input to the system. This embodiment of the invention has two separate computers because it is adapted for on-line use; that is, it is designed to monitor a fluid continuously flowing in a pipeline in an oil refinery or other industrial plant. Main computer 16 is located with the laser and spectrograph in a cabinet near the pipeline. Com computer 17 and display 18 are located in a central control room where operation of the oil refinery or plant is closely monitored. Com computer 17 is provided to facilitate communication between the control room and the pipeline location and to drive display 18.

Figure 3:
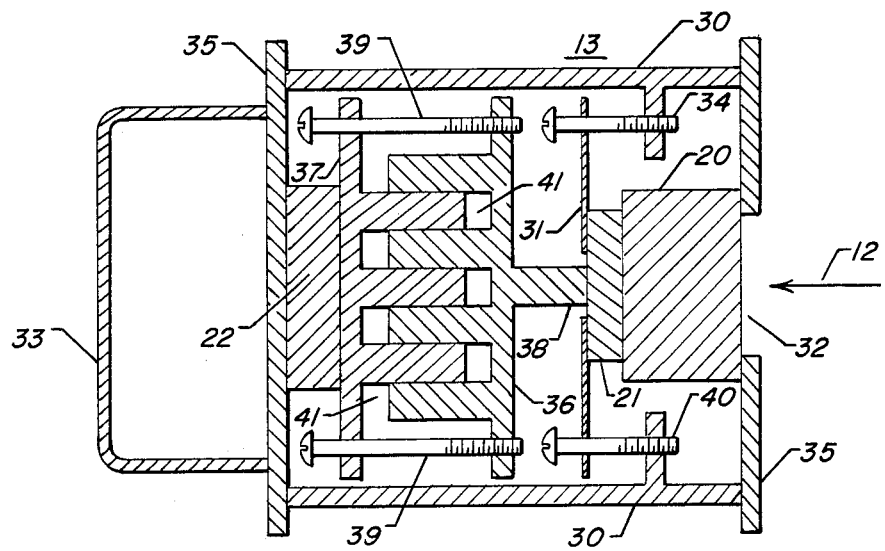
FIG. 3 is a simplified sketch of the detector of FIG. 1 drawn as if it were a cross-sectional view. It is not an engineering drawing and is not complete, but is intended only as an aid in understanding the invention.

Continuing with the description of this embodiment and now referring to FIG. 2, the major functional components of detector 13 and detector controller 14 can be seen. Image intensifier 20 senses the spectrum resolved by spectrograph 11 (FIG. 1) as denoted by arrow 12 (FIGS. 1, 2, and 3). The purpose of image intensifier 20 is to increase the intensity of the spectrum so that it may be sensed by photo-diode array package 21, in a reasonably short time, since the intensity of Raman scattered light is low. Image intensifier 20 may be viewed as a device which magnifies light but does not change any other characteristic of the light; for example, for each photon entering the intensifier, 20 photons may be emitted from it. The array package is capable of sensing a spectrum without intensification, but the analysis time would have to be increased. The intensifier is manufactured by Ni-Tec of Niles, Ill. Photodiode array package 21 senses the intensified spectrum and converts it into a series of electrical signals. Sensing is accomplished by integration of the light striking the array over a short period of time. The array consists of 1024 linear silicon diode elements, each of which is responsive separately to the number of photons striking it. The elements are vertically oriented and side-by-side, each element having a vertical dimension of about 2.5 mm and a horizontal dimension of about 0.025 mm. Each element senses a narrow vertical slice of the spectrum band. The total width of the 1024 elements is approximately 25.6 mm. The cover plates of both the intensifier and the array package which are adjacent to one another, comprise fiber optic bundles. Use of the bundles is an important feature, as will be explained later. The array package is manufactured by E. G. and G. Reticon (Model 1024SF) of Sunnyvale, Calif. Thermo-electric cooler 22 is provided to cool photodiode array package 21 and other components of the detector. It is supplied by Borg-Warner Thermoelectrics. The balance of the functional blocks of FIG. 2 are self-explanatory to those skilled in the art, comprising electronic apparatus for accomplishing the functions of providing electric power to operate the converting apparatus, communicating with a computer, controlling temperature of the converting apparatus, controlling read-out of said intermittent electrical signals, conditioning signals, and controlling operation of the converting apparatus.

Additional description of photo-diode array package 21 is as follows. Each diode element, or cell, consists of a photo-diode and a dummy diode, both with an associated storage capacitance. These diodes are connected through MOS multiplex switches to video and dummy recharge lines. The multiplex switches are turned on and off in sequence by shift register scanning circuits, thereby periodically recharging each cell to 5 volts and storing a charge on its capacitance. The shift registers are driven by multiphase clocks with periodic start pulses being introduced to initiate each scan of the cells. Integration time is the interval between start pulses. During this integration time, the charge on each capacitor is removed by the reverse current flowing in its associated diode. There are two components to the reverse current, photocurrent and dark current leakage. Photocurrent results from the light falling on the photodiode. The dummy diode is not exposed to light and its purpose is to permit dark current leakage and other false information to be subtracted out. Use of the output of the dummy diodes is optional in the practice of the invention, as is explained herein. If the dummy diode output is used, the subtraction is accomplished "on the fly". During read-out, or scan, of the diodes, the outputs of both the photo-diodes and the dummy diodes are sent to a differential amplifier which is part of the detector electronics and which accomplishes the subtraction.

The significant features of detector 13 are shown in FIG. 3. Image intensifier 20 is mounted in metal housing 30. Opening 32 is provided so that intensifier 20 may receive the spectrum resolved by spectrograph 11. Opening 32 is covered by a light-transparent material (not shown). In an alternative arrangement, filter 9 (FIG. 1) could be placed at opening 32. An elastic silicone compound (not shown) fills a portion of the space between housing 30 and the circumference of image intensifier 20. Photodiode array package 21 is mounted on diode board 31, which provides foil tracks to serve as conductors from the pins of photo-diode array package 21 in addition to serving as a holder for the array package. Wires (not shown) are soldered to the foil tracks to connect array package 21 with a preamplifier and signal enhancer, which is physically located inside electronics enclosure 33 attached to the back of housing 30. Referring briefly to FIG. 2, the wires are represented by dashed line 23. Returning to FIG. 3, diode board 31 is held in place by screws denoted 34 and 40. Cylindrical springs (not shown) enclose screws 34 and 40 between diode board 31 and the heads of the screws such that pressure is exerted on the diode board which urges photo-diode array package 21 into contact with intensifier 20. The intensifier and array package must be in alignment so that the spectrum image is properly oriented on the diodes. Adjustment of diode board 31 in its own plane in a horizontal direction is provided by means of placement of screw 34. (Note that the diode board is shown rotated by 90° in FIG. 3 for ease of drawing.) There are three holes on the diode board at one end, only one of which is used at a time for screw 34. There are three tapped holes in the body of the housing to accept screw 34, one corresponding to each hole of the diode board. Both sets of holes are arranged so that each set falls on a single straight line, but the straight lines form an angle with one another, so that moving screw 34 from one position to another causes the diode board to move horizontally. A horizontal slot (or slots) at the other end of the board accommodates the movement, the screw 40 at that end being placed in the slot (or slots). If there is a vertical misalignment between the intensifier and array package, a mirror in spectrograph 12 can be adjusted to shift the image in the vertical direction. The intensifier is large enough to accommodate the image shift. The intensifier can also be rotated with respect to the array package; this is advantageous, for example, if a portion of the intensifier is suspected of malfunction. Between intensifier 20 and array package 21 is a coating of refractive index matching fluid (not shown) of refractive index 1.5. The fluid, which may be described as a grease, is supplied by Cargille Laboratories of Cedar Grove, N.J.

The arrangement of intensifier 20 and diode array 21 and the use of an index matching fluid is quite significant. Light emitted from the interior of the intensifier passes through the fiber optic bundle which comprises the intensifier back cover plate, through the index matching fluid, and through the fiber optic bundle comprising the cover plate of the diode array package. This arrangement avoids the loss of resolution and intensity which would take place were the light comprising the spectrum to pass through media having significantly different indices of refraction, as the index fluid was chosen to have an index of refraction substantially the same as that of the fiber optic bundles. Detectors which might have been purchased utilize a lens to focus light onto a sensing device, such as the diode array package; use of a lens causes a loss of sharpness. An analogy involving viewing an image on a television screen is helpful in appreciating the benefits of the above-described arrangement. In a darkened room, a wall parallel to a TV screen will show a blur of light. If an appropriate lens is placed between the screen and the wall, an image will be seen on the wall. The image on the wall will be dimmer and less sharp than the image on the TV screen. Likewise, the image on the array package would be degraded if a lens were used between the array package and intensifier. If it were possible to place tubes having light-impenetrable walls and not susceptible to internal reflections between each "dot" of a TV screen and points on the retina of a viewer's eye, the image seen would be much sharper and more intense than that seen when the image is focused on the retina by the cornea (lens) of the eye after the light has passed through the air between TV set and eye. The tubing, of course, is analogous to the light-conducting fibers of a fiber optic bundle. Thus the arrangement of the two fiber optic bundles with a coating of index fluid and butted against each other serves to transfer the spectrum directly to the diodes, with little loss of intensity and little loss of resolution or spreading of the light. Impingement on more diodes solely because of the optical system is minimized.

Returning to FIG. 3, thermo-electric cooler 22 is mounted on backplate 35 of housing 30. Provided to serve as a thermal path between cooler 22 and array package 21 are cold plates 36 and 37. The cold plates are also essential in providing a thermal mass and a thermal lag in the system so that the detector can be maintained at a constant temperature with a variation of only about 0.1 degree Celsius. Each of the cold plates is a circular flat disc approximately ⅛-inch thick whose diameter is less than the inside diameter of housing 30. Cold plate 37 has a ridge which is rectangular in cross-section, extends along an entire diameter of the plate, and is about ¼-inch thick and ¼-inch high. Cold plate 37 also has several additional similar ridges parallel to the central ridge, and extending to the perimeter of the disc. Cold plate 36 has a series of similar ridges positioned so that they interleave with the ridges of cold plate 37. The dimensions of the ridges on the two cold plates are such that there is substantial contact between the two plates. The cold plates are connected together by screws 39. The portion of the screws between the cold plates are enclosed by cylindrical springs (not shown). Since screws 39 are threaded only so as to engage threads in cold plate 36, the springs urge the cold plates apart from one another. Cold plate 36 has a portion which extends from the side opposite the ridges toward array package 21. This portion is denoted cold finger 38. An opening is provided in diode board 31 so that cold finger 38 may touch array package 21. The space around cold finger 38 contains pins and wiring associated with diode board 31. It can now be seen that the width of the assembly formed by the cold plates and screws is variable and that the springs (not shown) around screws 39 cause cold plate 37 to bear against cooler 22 and cold plate 36 to bear against array package 21. Though not shown in FIG. 3, detector 13 is sealed and provided with an air purge so that it is suitable for use in areas where explosion-proof equipment is required. The laser housing is also sealed and purged. More specifically, the PNA analyzer meets the requirements of the National Electric Code for use in Class I, Division 1, Groups C and D areas.

The detector/detector controller may be viewed as a device for converting a visible light pattern to digital form, that is, converting the frequency and intensity information contained in the light pattern to information expressed in a computer-compatible "language" or computer-intelligible electrical impulses. That there are two separate devices termed detector and detector controller is a result of convenience in packaging and the two packages may be viewed as one device. In the development program of the analyzer, it was attempted to incorporate commercially available detector devices, but all had shortcomings. Since the amount of Raman-scattered light is quite small and it is desired to use a relatively low-power light source, the detector must be quite sensitive to very small differences in intensity as well as being capable of recording low intensity light accurately. It must be capable of reading a relatively large area, since a spectrum is resolved into a band which covers a particular area and the band area is considered large by those familiar with applicable sensing apparatus. It must be capable of high resolution, that is, breaking the area read into a sufficient number of discrete and separate elements such that the distinct spectral lines can be perceived. It must be capable of use in an oil refinery environment or other industrial area, outside of temperature controlled areas. This requirement includes ease of maintenance and a rugged design. In the detector of this invention, the intensifier and the diode array package may be independently replaced. This is an important feature in that each item is costly. The thermo-electric cooler is also capable of independent replacement. The provisions for adjustment of the diode board in its own plane, mentioned earlier, are necessary to align the two components, so that all of the photo-diode elements receive photons from the intensifier. The provisions for adjustment in a direction normal to the plane it lies in permit the diode array to be positioned directly at the point at which photons are emitted from the intensifier.

In the PNA analyzer, the programs for computers 16 and 17 are in the form of firmware, that is, contained in chips, as is all required operating data. The term "computer" or "computing means" as used herein is meant to refer broadly to a collection of electronics devices used to perform functions such as collecting, storing, comparing, manipulating, and transmitting data and information. A PNA analyzer is in the form of two modules. One module contains com computer 17 and its associated control panel and display 18 while the other, the main module, contains the balance of the apparatus described above plus additonal apparatus as required, such as standard commercial refrigeration apparatus to maintain a constant temperature. The main module is located near a process pipeline in a refinery or plant, as mentioned above. Connections are provided for a flowing sample stream to enter and exit the module (whereupon it will flow through sample cell 6). A sample handling system may be included with the main module or may be separate from it. Such systems are quite familiar to those skilled in the art and contain components such as a sample reservoir, pumps, pressure safety valves, flow metering devices, pressure regulators, and inert gas blanketing apparatus on an as-needed by the particular application basis. In addition to its more sophisticated functions described herein, computer 16 will perform a number of routine monitoring functions. For example, temperature sensors will be provided to sense an excessively high temperature in the refrigerated main module and at laser 26. These sensors will provide signals to computer 16 which will then cause an alarm on the associated control panel to be activated upon occurrence of high temperatures. These routine functions need not be described here, as it becomes clear to one assembling the apparatus of the invention that certain parameters should be monitored. Choice of parameters to be monitored is dependent upon the particular equipment used in the analyzing apparatus and the use to which the apparatus is to be put.

Description of the method and apparatus of the invention is continued, with reference to the PNA analyzer embodiment. As mentioned above, the Raman spectrum of a sample is recorded in computer 16. More exactly, it is only a portion of the Raman spectrum, as the anti-Stokes lines are removed by filter 9 and there may be very low wave number lines which exceed the capacity of the apparatus. Also, additional portions of the sample spectrum transmitted to the computer are removed in the computer, as will be described. It is convenient and common to visualize spectra expressed in the form of curves, such as those of FIG. 4, in which intensity is plotted against wave length. More commonly, wave number is used in place of wave length, where wave number is the reciprocal of delta wave length, delta referring to the distance between the exciting wave length and the wave length of interest. The description herein refers to manipulation of curves and spectra somewhat interchangeably; it is to be understood that the curves are representative of spectra. Locations of particular peaks of a sample spectrum and their heights are compared to peak locations and heights of known substance spectra, the known spectra having previously been recorded from samples whose compositions were known. Generally, when the peak locations coincide, or are at substantially the same wave lengths, it can be concluded that the sample contains the known substances. The quantities of components of the sample are determined by comparing peak areas. As is explained in more detail herein, the term peak is often used in referring to a spectral response region and peak height may be replaced by peak area or spectral response region area.

Each spectrum recorded in the computer is adjusted to eliminate portions capable of affecting analysis accuracy, that is, false information. To eliminate portions comprised of sample fluorescence and stray photons, a baseline is established and that portion of the spectrum below the baseline is discarded, or ignored in accomplishing the analysis. A valley search method is used to establish a baseline. The lowest point in each of three areas, or windows, is determined. A window is located at each end of the spectrum and one in the middle. A provisional baseline is then drawn connecting the three points with two straight line segments. A search is then made for points of the spectrum curve which are below the provisional baseline. If any are found, the affected part of the provisional baseline is replaced by line segments connecting those points with the three initially found low points. Of course, there are alternative methods of establishing a baseline, including drawing an arbitrary line without reference to the data.

A background spectrum is obtained and stored in the computer. The background spectrum may be characterized as comprising amplifier dark count noise and ambient photons. It is obtained in the same manner as a sample spectrum but with shutter 4 closed so that the beam of photons is prevented from reaching the sample. The background spectrum is subtracted from the sample spectrum; at each frequency, the spectrum intensities are subtracted. As described above, photodiode array package 21 comprises 1024 light sensitive diodes, each paired with a dummy diode which is not light sensitive. The outputs of the dummy diodes may be subtracted from the outputs of the light sensitive diodes in order to correct for dark current and thus obtain a more accurate spectrum and analysis. The dark count noise component of a background spectrum serves substantially the same purpose as the dummy diode outputs. Either method or both methods may be used to adjust spectra.

In the PNA analyzer, a sample spectrum is not compared to a single reference spectrum in order to obtain an analysis. In effect, the sample spectrum is compared to a plurality of reference spectra. The reference spectra are used to construct a mathematical entity, which may loosely be termed a correlation, and then the correlation is used to determine the analysis of each unknown sample. To construct the PNA analyzer correlation, 28 known samples were used. Use of less than about 18 samples would have resulted in analyses of decreased accuracy and use of more than 28 samples would not have had a significant effect on the level of accuracy. The number of known samples which should be used in constructing a useful correlation is dependent on the nature of the spectra, the particular substances analyzed, and the accuracy desired. The minimum required number will become clear from the further description. It is preferred that the known samples used be blends rather than pure substances, as molecular interaction takes place when pure substances are blended which could result in a degradation of accuracy. A pure substance is defined for use herein as a substance which is determined by the analysis. To illustrate, in the case of the PNA analyzer, a sample of paraffin alone is a pure component, while a sample containing paraffins and aromatics is a blend. In constructing a correlation, values of a set of coefficients are determined. It is the coefficients which are then used in accomplishing analysis of unknowns.

The method embodied in the PNA analyzer may be described as comprising: (a) producing a beam of photons which is substantially monochromatic and impinges on the unknown sample; (b) collecting photons scattered by the unknown sample into a stream of scattered photons; (c) resolving the photon stream into its component frequencies to form a Raman spectrum of the unknown sample; (d) providing said unknown sample Raman spectrum to a computer; (e) providing to the computer reference spectra obtained in the same manner as said unknown spectrum, where the reference spectra are of reference samples whose quantitative composition is known and where each reference sample is comprised of at least one of said preselected substances; and, (f) identifying substances present in the unknown sample by comparing said unknown spectrum to the reference spectra, said comparison being accomplished by utilizing the computer and a method comprising the following steps: (i) inspecting the reference spectra and selecting a plurality of separate spectral analysis regions; (ii) determining the areas of the selected regions for each reference spectrum and for the unknown spectrum; (iii) establishing a relationship between said reference spectra region areas and concentrations of said preselected substances in said reference samples; and, (iv) determining the concentrations of said preselected substances in said unknown sample by applying the relationship established in step (f)(iii) to the unknown spectrum region areas.

Figure 4:
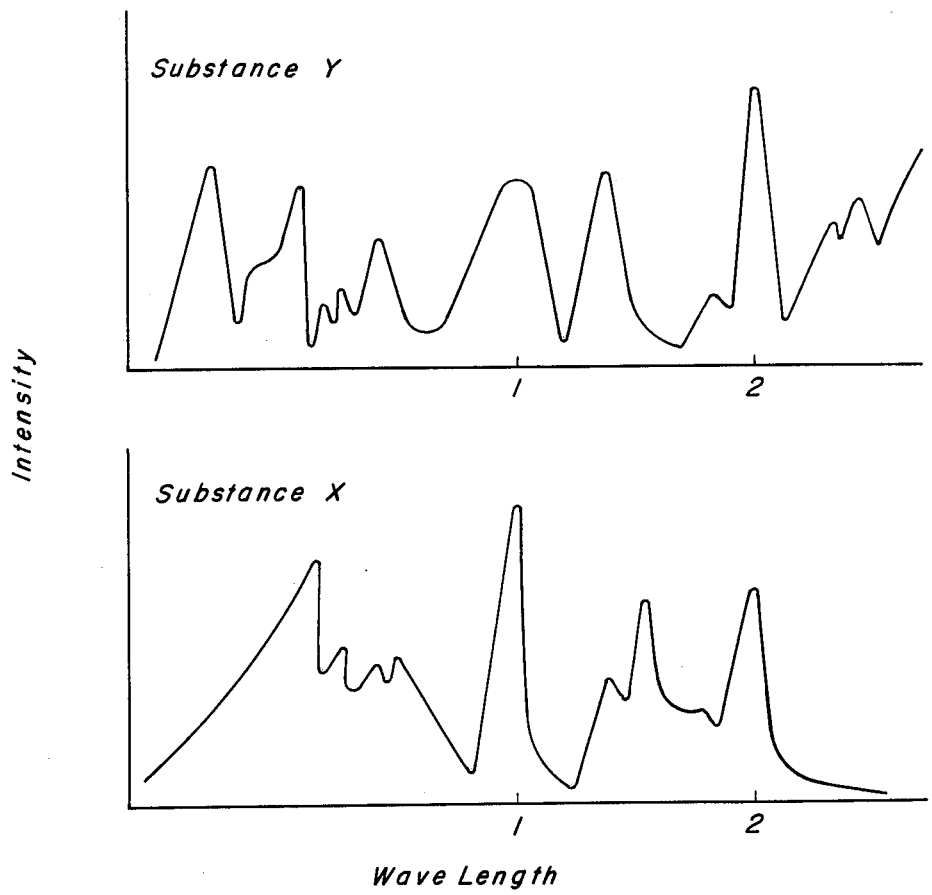
FIG. 4 is a representation of spectra of two different substances, which has been arbitrarily drawn for the purpose of illustration.

A simple illustration of a method of determining and using a correlation will now be presented to aid in understanding the invention. The purpose of the exemplary analysis will be to analyze samples containing substances X and Y. In FIG. 4, two reference spectrum curves are shown, one recorded from a sample of pure X and one recorded from a sample of pure Y. Consider that a spectrum has been recorded from a sample containing both X and Y and is desired to determine their concentrations in this unknown sample. To determine the correlation, the two known spectra are inspected and two peak locations are chosen, denoted 1 and 2 on FIG. 4. Each spectra has a peak at each location. The unknown sample spectrum will also have peaks at these two locations. Each substance contributes to the area of each of the two peaks of the unknown spectrum. The concentration of X in the unknown is proportional to the area of peak 1 and the area of peak 2 and the concentration of Y is proportional to the areas. Two equations can be written for any unknown containing X and Y:

$$X = C_{1X}A_1 + C_{2X}A_2,$$

and $$Y = C_{1Y}A_1 + C_{2Y}A_2,$$

where
X = concentration fraction of X,
Y = concentration fraction of Y,
$A_1$ = area fraction of peak 1, i.e., area of peak 1 divided by area of peaks 1 and 2,
$A_2$ = area fraction of peak 2, similarly defined,
$C_{1X}$ = a coefficient associated with the contribution of substance X to peak 1,
$C_{2Y}$ = a coefficient associated with the contribution of substance Y to peak 2, and
$C_{2X}$ and $C_{1Y}$ are similarly defined.

Peak areas are measured and $A_1$ and $A_2$ are calculated. In order to calculate X and Y, the four coefficients must be known. The coefficients are determined by writing and solving the above two equations for the pure X spectrum and the pure Y spectrum. Noting that the concentration of Y in the sample of pure X is 0 and the concentration of X in the sample of pure X is 1 and that similar relationships exist for the sample of pure Y, the 4 equations are:

pure X spectrum $$C_{1X}A_{X1} + C_{2X}A_{X2} = 1$$

$$C_{1Y}A_{X1} + C_{2Y}A_{X2} = 0$$

pure Y spectrum $$C_{1X}A_{Y1} + C_{2X}A_{Y2} = 0$$

$$C_{1Y}A_{Y1} + C_{2Y}A_{Y2} = 1.$$

The X and Y subscripts are added to the area fractions to indicate which curve the area fraction refers to, pure X or pure Y. After the peak areas are measured and the area fractions numbers inserted, there are four equations and four unknowns, so the equations are solved for the four coefficients. The coefficients are then inserted into the two equations for the unknown spectrum and the equations solved for X and Y. Additional samples of mixtures of X and Y can be analyzed using the same correlation coefficients.

The broad method of the above simple example can be described as follows: (a) selecting a number of spectral analysis regions equal to the number of said preselected substances; (b) determining the areas of the selected regions for each reference spectrum and for the unknown spectrum and calculating area fractions; (c) establishing a set of equations for each reference sample where the number of equations in each set is equal to the number of said preselected substances and each equation describes the concentration of one preselected substance in terms of its contributions to region areas, each equation having the form $$X = C_{1x}A_1 + C_{2x}A_2 + \ldots + C_{nx}A_n,$$

where X represents the concentration fraction of the preselected substance, $A_1, A_2, \ldots A_n$ are area fractions of the selected regions of the spectrum of the reference sample where n equals the number of regions, and $C_{1x}, C_{2x}, \ldots C_{nx}$ are coefficients associated with the contributions of the preselected substances to the regions; (d) solving all of the equations established in step (c) for said coefficients; (e) establishing one set of equations for the unknown sample as was done in step (c) for each reference sample; and, (f) solving said unknown sample equations for the concentrations of the preselected substances, using the coefficients determined in step (d).

To construct the PNA analyzer correlation, six peak locations were chosen. The use of the terms peak and peak location is common and used herein. Peak location is usually expressed by a particular wave length or wave number; for example, as shown by points 1 and 2 in FIG. 4. Peak location may be expressed by means of a wave number range, thus indicating the boundaries of the peak. This range may be referred to as a spectral analysis region. A spectral analysis region may be defined as a portion of a spectrum, or spectrum curve, where two wave numbers are used to denote the boundaries of the portion. The use of a spectral analysis region removes ambiguity where there are sub-peaks, additional peaks below the main peak, and/or in dealing with samples in which no peak appears. It should be understood that spectral analysis regions were used in the PNA analysis and may be used in other applications even though the common terminology of peak location is used. In general, as used herein the term peak is interchangeable with the term spectral analysis region. It may be said that a peak location is used as a means of referring to a spectral analysis region. Spectral intensity is commonly expressed in terms of peak height and/or peak area. When the term spectral analysis region is used, intensity is usually expressed in terms of area of the region, though it can be expressed in terms of the height of the highest peak of the region.

The mathematics used to construct the PNA analyzer correlation are more sophisticated than in the above example; the method may be characterized as a multiple linear regression with a least squares fit. Matrix algebra is used. The starting point is the equation:

area fraction (sample, peak) × coefficient (peak, component) = concentration fraction (sample, component).

Each of the components of the equation is a matrix arranged in accordance with the items in parentheses. For example, the area fraction component may be written as a 28 by 6 matrix containing 168 area fractions.

The area fractions are determined by measuring the area of each chosen peak for each of the 28 spectra. Of course, this is done in the computer. The concentration fractions are known because each of the 28 samples had previously been analyzed by other means (described below). Both sides of the equation are multiplied by the transpose of the area fraction matrix in order to satisfy the least squares criteria. The resulting expression is then solved for the coefficient matrix. To complete an analysis for the amounts of P, N, and A in an unknown sample, the above equation is solved for concentration fractions, using the above-obtained correlation coefficient matrix and area fractions determined from the unknown spectrum. In summary, the method of providing reference information to the PNA analyzer comprises (a) recording spectra of a number of samples whose analyses is known and representative of the range of unknown samples which it is desired to analyze using the PNA analyzer, (b) inspecting these spectra to choose a number of peak locations, (c) measuring the area of the chosen peaks, computing area fractions, and arranging the area fractions in matrix form, (d) creating a matrix from the known sample analyses, and (e) accomplishing a multiple linear regression with a least squares fit using matrix algebra.

A more detailed summary of the above described method is as follows. The relationship is established and said concentrations determined by: (a) expressing said reference sample concentrations in terms of concentration fractions and arranging the concentration fractions in a concentration fraction matrix, according to said reference samples and said preselected substances; (b) calculating area fractions from said reference spectra region areas and arranging the area fractions into an area fraction matrix, according to said reference samples and the selected regions; (c) determining a transpose matrix, which is the transpose of the area fraction matrix; (d) forming a mathematical relationship using said matrices as follows:

$$\frac{\text{concentration fraction matrix} \times \text{tranpose matrix}}{\text{area fraction matrix} \times \text{tranpose matrix}};$$

(e) solving said mathematical quantity to yield a matrix, which consists of correlation coefficients, arranged according to the selected regions and said preselected substances; (f) calculating area fractions from said unknown spectrum region areas and arranging the area fractions in a matrix; and, (g) multiplying said correlation coefficients matrix by the matrix formed of said unknown spectrum area fractions to obtain a product which is a concentration fraction matrix which expresses the concentrations of the preselected substances in said unknown sample.

Those familiar with the above described methods and applied linear algebra will appreciate that there are different methods of processing reference data for use in the analyzer of this invention; these methods are considered to be within the scope of this invention. It is readily seen that less data than indicated above could have been used in the PNA analyzer correlation. For example, three peaks instead of six are mathematically sufficient. However, upon inspection of known sample spectra, it was believed that better accuracy would be obtainable by using more than the minimum number. Note also that a least squares method was used because more data than the minimum amount was placed in the correlation. In a different correlation which was prepared, which can be used in place of the PNA correlation and thereby convert the apparatus to an Aromatics analyzer, four peaks, or peak locations, were used for a four substance analysis. There was no need to overdetermine, as was done with the PNA correlation, because the peak overlap, as determined from the known sample spectra, was relatively small. Sixteen samples were used to construct the Aromatics analyzer correlation. This analyzer provides the amounts of paraxylene, orthoxylene, metaxylene, and ethylbenzene in a sample and is useful in hydrocarbon processing operations, particularly in the operation of an aromatics complex. An aromatics complex is a part of an oil refinery in which naphtha is converted into aromatic intermediates such as benzene, paraxylene, and orthoxylene. These intermediates are then further processed outside the aromatics complex to obtain such products as nylon, styrene, phenol, phthalic anhydride, polyesters, surfactants, and detergents.

Where to place the boundaries of spectral response regions becomes clear upon inspecting the spectra. Areas containing the highest peaks are usually chosen. Areas containing easily identifiable features are desirable. Of course, areas which are flat or devoid of unique features are not chosen.

An instantaneous analysis is not available from the apparatus of the invention; a finite time period, which may be very small, is required to complete an analysis. The major determinants of time required for an analysis are time required to collect scattered photons, or allow the Raman-scattered light to affect the diode array, and the number of times the diode array is scanned to read out data, or the number of sensing periods. In the PNA analyzer, it usually requires about 5 to 10 seconds for the diode discharge step, that is, the step of sensing photons to accumulate data which is read out in a single scan. The time period is established by the apparatus. Each time the apparatus is powered-up and a sample provided for analysis, a test sensing period automatically takes place, in which photons are collected until one or several diodes sensing a peak reaches about 95% of its saturation value. The time period required to reach 95% is established as the length of a sensing period. A check test sensing period takes place before each spectrum is recorded. In a check test sensing period, the time interval is measured as in a test sensing period; however, the sensing period length is not changed unless the check test sensing period interval falls outside of the test sensing period interval plus or minus predetermined values. For each spectrum recorded in the PNA analyzer, data from 24 sensing periods and scan is used. Thus, the recorded spectrum is actually an average of 24 spectra. Of course, it is possible to use a spectrum resulting from one sensing period and scan. As used herein, the term "spectrum" means a spectrum derived from a selected number of sensing periods, which may be one or any other greater number. The number of sensing periods used to obtain a spectrum in any particular analysis is easily established by reference to the goals of the analysis and the character of the spectra.

The time period required to accomplish a PNA analysis is about 2 to 4 minutes. Twenty-four sensing periods of 5 to 10 seconds each require 2 to 4 minutes. Since scanning, data transmission, calculation, and other functions are carried out very quickly, it can be seen that a sample can be analyzed in little more than 2 to 4 minutes. The dummy spectra do not affect this time period, due to the manner in which the data is processed, as is discussed above. The adjustment of each spectrum consisting of establishing a baseline and subtracting, discussed above, does not materially affect this time period, since it is accomplished in the computer. Collection of the background spectrum discussed above requires the same time period as a sample spectrum. If used, a background spectrum is taken when the analyzer is powered-up and used to adjust each sample spectrum taken thereafter until there is a change in the sensing period length, in which case another background spectrum is taken. Since the PNA analyzer is designed for on-line use, an analysis is an average of the flowing stream composition for a 2-minute period. Of course, should it be desired to obtain an analysis of the stream at a particular moment, flow through the sample cell can be stopped for the 2-minute period. By using a single sensing period, the time to accomplish a PNA analysis can be cut to about 5 to 10 seconds.

The known sample analyses used to construct the PNA analyzer correlation were obtained by use of the method of analysis described in ASTM D1319, D1218, and a proprietary standard method which provides the same information as D1218. Those familiar with the ASTM methods, which are very widely utilized, will readily appreciate the importance of the present invention in accomplishing just this one type of analysis. Briefly, to obtain the saturates (P and N) content and the A content of a sample using ASTM D1319, sample is introduced to a long silica gel column, along with a fluorescent dye. Under ultraviolet light, two separate bands, one containing saturates and one containing aromatics, can be seen. Volume percent aromatics is determined by measuring the band lengths. The hydrocarbon sample is then eluted from the silica gel column by means of an alcohol, which preferentially adheres to the silica gel, displacing hydrocarbons. This procedure requires as long as 8 hours to complete. In D1218, the refractive index and density of the saturates fraction from the silica gel column are measured and used to determine the amounts of paraffins and naphthenes present in the sample. This requires about 1 hour. As an alternative, the saturates may be analyzed by means of a proprietary standard method which utilizes gas chromatography.

Data illustrative of the performance of the methods and apparatus of this invention are presented below. The first set of data consists of PNA analyses of 21 samples of reformer charge stock gathered from refineries throughout the U.S. Each sample was analyzed using both the present invention and the above-mentioned standard method (STD). The apparatus of the invention was not precisely that described in detail herein, but an earlier developmental prototype. The concentrations of P, N, and A are expressed in volume percent.

| Sample No. | Component | STD. | Invention | Difference |
|---|---|---|---|---|
| 1 | P | 68.90 | 69.95 | −1.05 |
|   | N | 22.30 | 20.50 | 1.80 |
|   | A | 8.80 | 9.55 | −0.75 |
| 2 | P | 64.80 | 63.59 | 1.21 |
|   | N | 22.50 | 23.41 | −0.91 |
|   | A | 12.70 | 13.01 | −0.31 |
| 3 | P | 47.10 | 49.21 | −2.11 |
|   | N | 44.70 | 42.61 | 2.09 |
|   | A | 8.20 | 8.18 | 0.02 |
| 4 | P | 60.90 | 61.30 | −0.40 |
|   | N | 16.40 | 16.00 | 0.40 |
|   | A | 22.70 | 22.70 | 0.00 |
| 5 | P | 58.50 | 58.59 | −0.09 |
|   | N | 25.50 | 26.73 | −1.23 |
|   | A | 16.00 | 14.68 | 1.32 |
| 6 | P | 59.70 | 60.83 | −1.13 |
|   | N | 22.70 | 21.28 | 1.42 |
|   | A | 17.60 | 17.90 | −0.30 |
| 7 | P | 53.40 | 51.92 | 1.48 |
|   | N | 36.10 | 35.45 | 0.65 |
|   | A | 10.50 | 12.63 | −2.13 |
| 8 | P | 54.50 | 54.84 | −0.34 |
|   | N | 34.40 | 33.06 | 1.34 |
|   | A | 11.10 | 12.11 | −1.01 |
| 9 | P | 66.10 | 64.88 | 1.22 |
|   | N | 20.50 | 21.45 | −0.95 |
|   | A | 13.40 | 13.67 | −0.27 |
| 10 | P | 47.80 | 50.86 | −3.06 |
|   | N | 44.70 | 41.40 | 3.30 |
|   | A | 7.50 | 7.74 | −0.24 |
| 11 | P | 61.90 | 61.52 | 0.38 |
|   | N | 28.40 | 29.10 | −0.70 |
|   | A | 9.70 | 9.39 | 0.31 |
| 12 | P | 66.20 | 67.10 | −0.90 |
|   | N | 19.90 | 19.32 | 0.58 |
|   | A | 13.90 | 13.59 | 0.31 |
| 13 | P | 48.50 | 50.05 | −1.55 |
|   | N | 39.60 | 38.94 | 0.66 |
|   | A | 11.90 | 11.02 | 0.88 |
| 14 | P | 50.40 | 49.62 | 0.78 |
|   | N | 37.90 | 39.43 | −1.53 |
|   | A | 11.70 | 10.95 | 0.75 |
| 15 | P | 60.10 | 60.65 | −0.55 |
|   | N | 34.70 | 33.51 | 1.19 |
|   | A* | 5.20 | 5.85 | −0.65 |
| 16 | P | 51.80 | 50.91 | 0.89 |
|   | N | 38.00 | 38.93 | −0.93 |
|   | A | 10.20 | 10.17 | 0.03 |
| 17 | P | 60.30 | 55.54 | 4.76 |
|   | N | 31.70 | 36.71 | −5.01 |
|   | A | 8.00 | 7.75 | 0.25 |
| 18 | P | 63.80 | 64.29 | −0.49 |
|   | N | 27.90 | 27.85 | 0.05 |
|   | A | 8.30 | 7.86 | 0.44 |
| 19 | P | 67.10 | 69.09 | −1.99 |
|   | N | 22.60 | 20.84 | 1.76 |
|   | A | 10.30 | 10.07 | 0.23 |
| 20 | P | 65.90 | 62.70 | 3.20 |
|   | N | 22.50 | 26.11 | −3.61 |
|   | A | 11.60 | 11.20 | 0.40 |
| 21 | P | 57.20 | 57.51 | −0.31 |
|   | N | 31.00 | 31.40 | −0.40 |
|   | A | 11.80 | 11.09 | 0.71 |

|  | P | N | A |
|---|---|---|---|
| Coefficient of correlation | 0.9655 | 0.9737 | 0.9812 |
| Standard error | 1.77 | 1.91 | 0.75 |

The coefficients of correlation presented immediately above are not the same as the correlation coefficients used in the practice of the invention; both the coefficients of correlation and the standard error are parameters commonly used in statistical analysis and familiar to those skilled in the art.

The following data was collected using the aromatics correlation discussed above with a developmental prototype apparatus to analyze blends prepared from pure compounds. Measured values are those volumetrically measured out before combination to form the samples. All the numbers are expressed in volume percent. Compound identification is as follows: P=paraxylene, M=metaxylene, O=orthoxylene, and E=ethylbenzene.

| Sample No. | Component | STD. | Invention | Difference |
|---|---|---|---|---|
| 23A | P | 25.0 | 24.8 | 0.20 |
|   | M | 25.0 | 25.2 | −0.20 |
|   | O | 25.0 | 24.9 | 0.10 |

-continued

| | | | | |
|---|---|---|---|---|
| | E | 25.0 | 25.0 | 0.00 |
| 23B | P | 50.0 | 50.1 | −0.10 |
| | M | 12.5 | 12.4 | 0.10 |
| | O | 25.0 | 25.4 | −0.40 |
| | E | 12.5 | 12.3 | 0.20 |
| 23C | P | 29.4 | 29.8 | −0.40 |
| | M | 58.8 | 59.0 | −0.20 |
| | O | 5.9 | 5.8 | 0.10 |
| | E | 5.9 | 5.8 | 0.10 |
| 23D | P | 13.9 | 14.1 | −0.20 |
| | M | 27.8 | 28.2 | −0.40 |
| | O | 55.6 | 55.0 | 0.60 |
| | E | 2.8 | 2.9 | −0.10 |
| 23AB | P | 37.5 | 38.0 | −0.50 |
| | M | 18.8 | 18.4 | 0.40 |
| | O | 25.0 | 24.6 | 0.40 |
| | E | 18.8 | 19.1 | −0.30 |
| 23BC | P | 39.7 | 39.0 | 0.70 |
| | M | 35.6 | 36.1 | −0.50 |
| | O | 15.5 | 15.1 | 0.40 |
| | E | 9.2 | 9.3 | −0.10 |
| 23CD | P | 21.6 | 21.4 | 0.20 |
| | M | 43.3 | 42.3 | 1.00 |
| | O | 30.8 | 31.4 | −0.60 |
| | E | | | |
| 23DA | P | 19.4 | 19.2 | 0.20 |
| | M | 26.4 | 26.4 | 0.00 |
| | O | 40.3 | 40.8 | −0.50 |
| | E | 13.9 | 13.6 | 0.30 |

| | P | M | O | E |
|---|---|---|---|---|
| Coefficient of correlation | 0.99948 | 0.99945 | 0.99954 | 0.99970 |
| Standard error | 0.42 | 0.52 | 0.49 | 0.20 |

The developmental prototype mentioned above which was used in collecting the data presented above was the forerunner of the embodiment of the invention called the PNA analyzer. Though the PNA analyzer described is considered the best mode, it is currently in the later stages of development and has not yet been used in constructing a correlation. A significant difference between the PNA analyzer and the developmental prototype is that a detector supplied by EG&G PAR was used. (Model 1420 Intensified Diode Array Detector with Model 1218 Detector Controller).

The term "PONA analysis" is frequently used in hydrocarbon refining, the O referring to olefins and the other letters having the same meaning as above. Usually though, all four substances are not present in the sample or of no interest and the laboratory reports only the items of interest. For example, the catalytic reformer feed upon which the PNA analyzer of the invention is utilized usually contains no or very little O. In analyzing gasolines, results are normally reported as saturates (P and N), O, and A. In this example, olefins are of particular interest because of their octane enhancing effect. Since the PNA analyzer is designed for on-line use with catalytic reformer feed, there is no purpose to be served in incorporating O into the correlation. However, there is no reason this cannot be done, so as to provide a PONA analyzer for use in a laboratory (a spectral analysis region has been chosen and correlation data accumulated).

An object of this invention is to provide a universal method and apparatus for qualitative and quantitative analysis utilizing the Raman effect. By universal is meant the capability of analyzing a wide variety of substances without having to specially adapt method and apparatus. The PNA analyzer described in detail herein can be converted to a different type of analyzer by providing it with a correlation developed for the substances of interest and possibly changing certain other operating parameters, such as the number of sensing periods, as discussed above. In a different embodiment of the invention, such as a laboratory version, the correlation and operating parameters need not be embodied in firmware, as in the PNA analyzer. A universal laboratory analyzer might contain a number of correlations and the operator might choose which one to use in analysis of each particular sample. Considerable work has been done using samples of various types of hydrocarbons and the apparatus of this invention; it is clear that the invention is well suited for various types of hydrocarbon analyses. A sufficient number of other substances have been run on the apparatus to conclude that correlations can be prepared for substantially every substance which exhibits a Raman spectrum and thus the invention can be characterized as universal within the meaning used herein. For example, in processes for the separation of sugars such as fructose and glucose from mixtures containing mono- and polysaccharides, a rapid analysis for glucose, fructose, and maltose is highly desirable. Sugar spectra are complex and have broad overlapping peaks. Though no region of the spectrum of sugars solutions was found which contained well resolved peaks of the three sugars, it is possible to construct a correlation and obtain sufficiently accurate analyses. Of course, there are a multitude of analysis methods and apparatus and each has its own areas of advantage. This invention is not claimed to replace all other methods but to provide means for utilizing the advantages of Raman spectroscopy and to take its place among the proven methods available in the field.

The sample containers mentioned above are suitable for samples in liquid and gaseous form. The invention is not limited to fluid samples, but can also be used for analysis of solid samples. It is a simple matter to replace a fluid sample container with means to hold a solid so that the laser beam impinges on the solid. Work was done from which it may be concluded that the methods and apparatus of the invention are suitable for use in analyzing solids. For example, certain hydrotreating catalysts impregnated by several different methods were studied. Differences in the spectra were relatable to concentrations of specific substances, such as nitrates and polymolybdates. The samples were in the form of cylindrical pellets. The laser beam impinged on the top plane, with the angle formed by the beam and the top surface being 25°. A line normal to the plane of the collection lens used would be perpendicular to the laser beam. As a precaution, the sample was rotated to avoid thermal decomposition, though this probably was not necessary. Other work was done which demonstrated that carbon deposits on the surface of a catalyst may be identified.

The applications of the invention discussed above have involved situations where it is known that a particular correlation should be used, that is, where it is expected that the sample will contain particular, or preselected, substances because of the location from which the sample was obtained, such as the PNA analysis on catalytic reformer feeds. It is also possible to analyze samples whose composition is totally unknown. There are a number of methods of approach. One method is accomplished by comparing an unknown spectrum with various known substance spectra from a library of spectra or data base and concluding that a known substance is present when the peak locations substantially coincide. In this method, the analyzer will first choose a number of the highest peaks, say the three highest peaks and note their locations. The peak locations could also be chosen by a human. The analyzer will then search the data base for spectra in which the three highest peaks are at the same locations, with appropriate numerical tolerances so that the analyzer will recognize that, for example, a peak at 1190 cm$^{-1}$ is the same as a peak at 1191 cm$^{-1}$. There may be two substances which have peaks at the same three locations. If so, the analyzer will look at the fourth highest peak of the unknown. If only one of the reference substances has a peak in this location (fourth highest), the analyzer will conclude that the unknown substance is that reference substance. It can be seen that there might not be enough peaks to make a determination. For example, the unknown spectrum might comprise only ten peaks and there may be several reference spectra having ten peaks in the same locations as the sample spectrum. This problem can be solved by the use of peak heights in addition to peak locations. Arbitrary numbers will be used to explain this by means of an example. Consider that the three highest peaks of the unknown are located at wave numbers 200, 300, and 400. Consider that there are two data base spectra, A and B, having peaks at the same locations. To compare further, look at the peak heights. Consider that the unknown peaks at 200, 300, and 400 have heights of 10, 8, and 6, respectively. If A has peak heights of 10, 9, and 6, respectively, and B has peak heights of 10, 8, and 6, it can be concluded that the unknown substance is substance B and cannot be substance A.

The above discussion has dealt with identification of unknown pure substances or situations where the data base contains a spectra which exactly corresponds with the unknown spectrum. This is a severe limitation. To deal with this limitation, reference samples can be "mixed" in the computer by constructing composite spectra from the spectra provided to the computer. Arbitrary numbers will be used to explain this method by means of a simple example. Assume that the data base consists only of pure substances. Assume that the data base has been searched and no pure substance spectra match has been found, leading to the conclusion that the unknown is a mixture. Assume that four pure compounds, A, B, C, and D, have been found in the data base which each exhibit peaks at wave numbers denoted point 1 and point 2, points at which the unknown exhibits peaks. If the components of the unknown are in the data base, they must be in the group of four which have been found. The peak heights are as follows, in arbitrary numbers.

| Substance | At Point 1 | At Point 2 |
|-----------|------------|------------|
| unknown   | 8          | 6          |
| A         | 10         | 8          |
| B         | 6          | 4          |
| C         | 16         | 8          |
| D         | 2          | 14         |

Start with a hypothesis that the unknown is a two-component mixture. The possible components are AB, AC, AD, BC, BD, CD. Let a, b, c, and d represent fractions of A, B, C, and D which might be present in the unknown. If the unknown is a mixture of A and B, equations for the contributions to the peaks by the substances must be satisfied. The equations are as follows:

$10a + 6b = 8$ $8a + 4b = 6.$

The numbers in the equations are the peak heights of A, B, and the unknown. Solving the equation yields a=0.5 and b=0.5, i.e., the unknown spectrum (considering only the two peaks) is the same as a spectrum of a substance consisting of 50% A and 50% B (considering only the two peaks). If the unknown could be a mixture of A and C, the equations are as follows:

$10a + 16c = 8$ $8a + 8c = 6.$

Solving these equations yields a negative number for a; thus the unknown cannot be a mixture of A and C. The other four possibilities can be checked in the same manner and if impossible solutions are found in each case, it can be concluded that the unknown is a mixture of A and B or mixture of three substances. If mixtures of three substances can be ruled out in a like manner as above, it can be concluded that the unknown is a mixture of A and B.

The above discussion may be summarized by the following description of a method for determining the composition of an unknown sample, such method comprising: (a) producing a beam of photons which is substantially monochromatic and impinges on the unknown sample; (b) collecting photons scattered by the unknown sample into a stream of scattered photons; (c) resolving the photon stream into its component frequencies to form a Raman spectrum of the unknown sample; (d) providing said unknown sample Raman spectrum to a computer; (e) providing to the computer reference spectra obtained in the same manner as said unknown spectrum, where the reference spectra are of reference samples whose composition is known; and, (f) identifying substances present in the unknown sample by comparing said unknown spectrum to the reference spectra, said comparison being accomplished by utilizing the computer and a method comprising the following steps: (i) inspecting the unknown spectrum and selecting a plurality of separate spectral analysis regions; (ii) determining a size characteristic associated with each region of the unknown spectrum; (iii) searching the reference spectra and choosing those spectra having in the selected regions features corresponding to those of the selected regions of the unknown spectrum and size characteristics substantially identical to those of the selected regions of the unknown spectrum; (iv) if more than one reference spectrum is chosen, repeating steps (f)(i), (f)(ii), and (f)(iii), selecting additional regions, until only one reference spectrum is chosen, the substances present in said one chosen reference spectrum being present in the unknown samples; (v) if no reference spectrum is chosen, establishing a number of working hypotheses, each hypothesis being that the unknown sample consists of a different combination of the reference samples which exhibited the spectra chosen to have features corresponding to those of the selected regions of the unknown spectrum; (vi) testing each working hypothesis by combining the spectra of the hypothesis to produce a single hypothetical spectrum and comparing it to the unknown spectrum; (vii) discarding each working hypothesis which is not substantially identical to the unknown spectrum; and, (viii) if more than one working hypothesis has not been discarded, repeating steps (f)(v) through (f)(viii), selecting additional regions, until only one working hypothesis has not been discarded, the unknown sample composition then being that of said one remaining working hypothesis.

Said testing may be accomplished by: (a) for each working hypothesis, establishing a set of equations consisting of one equation associated with each selected region of the unknown spectrum, which equation describes the area of the region in terms of concentrations of the reference samples and areas of reference spectra regions; and, (b) solving each set of equations to the extent mathematically possible and concluding that each working hypothesis whose set of equations cannot be completely solved or yields unreal numbers is not substantially identical to the unknown spectrum.

The equation associated with each region may be of the form $$X_1C_1 + X_2C_2 + \ldots + X_nC_n = A,$$

where $C_1, C_2, \ldots C_n$ = the concentration of the substance of reference samples $1, 2, \ldots n$ in the hypothetical combination of reference samples, $X_1, X_2, \ldots X_n$ = the areas of those regions in each of the reference spectra of the hypothetical combination, and $A$ = the area of the region of the unknown spectrum.

The size characteristic may be the height of the highest peak of the spectral response region or the area of the spectral response region.

A method which might be called stripping can be used. To illustrate, using the above example, form an initial working hypothesis that the unknown is a 50/50 mixture of A and B. Remove the A component of the peaks by subtracting 50% of the peak height of pure A, which is that part of the spectrum hypothesized as being attributable to A. Subtracting 5 and 4 from the 8 and 6 of the unknown yields 3 and 2. Doing the same thing for B leaves a flat spectrum (for those two peaks), since 50% of substance B peaks are 3 and 2. Since nothing is left of the peaks, it can be concluded that the unknown could be A and B.

It can be seen that there are other techniques, in addition to the above, which can be used to search a data base and identify an unknown sample. When the data base consists of pure substances, spectra of mixtures can be "constructed" in the computer of the analyzer, as described above, for comparison to an unknown. The data base may also comprise spectra of mixtures, if desired and available and these may be used to "construct" spectra for comparison. As mentioned above, it is preferable that known mixtures (blends) be used when the unknowns are mixtures (blends).

Another mode of analysis which can be accomplished by means of the present invention involves identification of source of an unknown sample. For example, a sample of crude oil whose origin is unknown could be identified as originating from a well in the Middle East instead of a well in Texas, given the appropriate data base.

There are many variations in apparatus within the scope of the present invention, examples of which are now mentioned. For a simple analysis in which the same substances are detected, a simple prism might be used to resolve the photon stream into its component frequencies and several detectors might be used, one for each wave length of interest. Filters could be used to remove wave lengths close to those being monitored. This approach would allow use of simpler and cheaper detectors and electronics. It is possible to eliminate means for resolving the photon stream by providing a number of filters, each of which allows photons of a specific wave length to pass. A complete spectrum could be recorded by placing each filter in turn in the stream of photons. In place of the quantity of filters, one or more variable band-pass interference filters could be used. With these filters, the peak transmission wave length is changed by varying the electrical potential applied across it. Other types of filters which might be used include Lyot filters, Fabry-Perot interferometer, and Christiansen filters. A tunable laser might be used, with the laser frequency adjusted over a band and detection accomplished at certain fixed frequencies.

We claim as our invention:

1. A method for determining the composition of an unknown sample comprising:
   (a) producing a beam of photons which is substantially monochromatic and impinges on the unknown sample;
   (b) collecting photons scattered by the unknown sample into a stream of scattered photons;
   (c) resolving the photon stream into its component frequencies to form a Raman spectrum of the unknown sample;
   (d) providing said unknown sample Raman spectrum to a computer;
   (e) providing to the computer reference spectra obtained in the same manner as said unknown spectrum, where the reference spectra are of reference samples whose composition is known; and,
   (f) identifying substances present in the unknown sample by comparing said unknown spectrum to the reference spectra, said comparison being accomplished by utilizing the computer and comprising the following steps:
      (i) inspecting the unknown spectrum and selecting a plurality of separate spectral analysis regions;
      (ii) determining a size characteristic associated with each of said spectral analysis regions of the unknown spectrum;
      (iii) searching the reference spectra and choosing those reference spectra having in the selected spectral analysis regions features corresponding to those of the selected spectral analysis regions of the unknown spectrum and size characteristics substantially identical to those of the selected spectral analysis regions of the unknown spectrum;
      (iv) if more than one reference spectrum is chosen, repeating steps (f)(i), (f)(ii), and (f)(iii), selecting additional spectral analysis regions, until only one reference spectrum is chosen, the substances present in said one chosen reference spectrum being present in the unknown samples;
      (v) if no reference spectrum is chosen, establishing a number of working hypotheses, each hypothesis being that the unknown sample consists of a different combination of the reference samples which exhibited the spectra chosen to have features corresponding to those of the selected spectral regions of the unknown spectrum;
      (vi) testing each working hypothesis by combining the spectra of the hypothesis to produce a single hypothetical spectrum and comparing it to the unknown spectrum;

(vii) discarding each working hypothesis which is not substantially identical to the unknown spectrum; and, (viii) if more than one working hypothesis has not been discarded, repeating steps (f)(v) through (f)(viii), selecting additonal spectral analysis regions, until only one working hypothesis has not been discarded, the unknown sample composition then being that of said one remaining working hypothesis.

2. The method of claim 1 further characterized in that said size characteristic is the height of the highest peak of the spectral analysis region.

3. The method of claim 1 further characterized in that said size characteristic is the area of the spectral analysis region.

4. The method of claim 1 further characterized with respect to step (f)(vi) in that said testing is accomplished by:

(a) for each working hypothesis, establishing a set of equations consisting of one equation associated with each selected region of the unknown spectrum, which equation describes the area of the region in terms of concentrations of the reference samples and areas of reference spectra regions; and, (b) attempting to solve each set of equations and concluding that each working hypothesis whose set of equations cannot be completely solved or yields unreal numbers is not substantially identical to the unknown spectrum.

5. The method of claim 4 further characterized in that said equation associated with each region is of the form $$X_1C_1 + X_2C_2 + \ldots + X_nC_n = A,$$

where $C_1, C_2, \ldots C_n$ = the concentration of the substance of reference samples 1, 2, ... n in the hypothetical combination of reference samples, $X_1, X_2, \ldots X_n$ = the areas of those regions in each of the reference spectra of the hypothetical combination, and A = the area of the region of the unknown spectrum.

6. A method for performing a quantitative analysis for preselected substances of an unknown sample comprising:

(a) producing a beam of photons which is substantially monochromatic and impinges on the unknown sample;

(b) collecting photons scattered by the unknown sample into a stream of scattered photons;

(c) resolving the photon stream into its component frequencies to form a Raman spectrum of the unknown sample;

(d) providing said unknown sample Raman spectrum to a computer;

(e) providing to the computer reference spectra obtained in the same manner as said unknown spectrum, where the reference spectra are of reference samples whose quantitative composition is known and where each reference sample is comprised of at least one of said preselected substances; and, (f) identifying substances present in the unknown sample by comparing said unknown spectrum to the reference spectra, said comparison being accomplished by utilizing the computer and comprising the following steps:

(i) inspecting the reference spectra and selecting a plurality of separate spectral analysis regions;

(ii) determining the areas of the selected regions for each reference spectrum and for the unknown spectrum;

(iii) establishing a relationship between said reference spectra region areas and concentrations of said preselected substances in said reference samples; and, (iv) determining the concentrations of said preselected substances in said unknown sample by applying the relationship established in step (f)(iii) to the unknown spectrum region areas.

7. The method of claim 6 further characterized with respect to step (f) in that said relationship is established and said concentrations determined by:

(a) selecting a number of spectral analysis regions equal to the number of said preselected substances;

(b) determining the areas of the selected regions for each reference spectrum and for the unknown spectrum and calculating area fractions for the reference spectra and for the unknown spectrum;

(c) establishing a set of equations for each reference sample where the number of equations in each set is equal to the number of said preselected substances and each equation describes the concentration of one preselected substance in terms of its contributions to region areas, each equation having the form $$X = C_{1x}A_1 + C_{2x}A_2 + \ldots + C_{nx}A_n,$$

where

X represents the concentration fraction of the preselected substance, $A_1, A_2, \ldots A_n$ are area fractions of the selected regions of the spectrum of the reference sample where n equals the number of regions, and $C_{1x}, C_{2x}, \ldots C_{nx}$ are coefficients associated with the contributions of the preselected substances to the regions;

(d) solving all of the equations established in step (c) for said coefficients;

(e) establishing one set of equations for the unknown sample as was done in step (c) for each reference sample; and, (f) solving said unknown sample equations for the concentrations of the preselected substances, using the coefficients determined in step (d).

8. The method of claim 6 further characterized with respect to steps (f)(iii) and (f)(iv) in that said relationship is established and said concentrations determined by:

(a) expressing said reference sample concentrations in terms of concentration fractions and arranging the concentration fractions in a concentration fraction matrix, according to said reference samples and said preselected substances;

(b) calculating area fractions from said reference spectra region areas and arranging the area fractions into an area fraction matrix, according to said reference samples and the selected regions;

(c) determining a transpose matrix, which is the transpose of the area fraction matrix;

(d) forming a mathematical quantity using said matrices, as follows:

$$\frac{\text{concentration fraction matrix} \times \text{tranpose matrix}}{\text{area fraction matrix} \times \text{tranpose matrix}};$$

(e) solving said mathematical quantity to yield a matrix, which consists of correlation coefficients, arranged according to the selected regions and said preselected substances;
(f) calculating area fractions from said unknown spectrum region areas and arranging the area fractions in a matrix; and,
(g) multiplying said correlation coefficient matrix by the matrix formed of said unknown spectrum area fractions to obtain a product which is a concentration fraction matrix which expresses the concentrations of the preselected substances in said unknown sample.

9. The method of claim 6 further characterized in that the substances comprising said unknown sample are paraffins, naphthenes, and aromatics.

10. The method of claim 6 further characterized in that said beam of photons is from a laser source.

11. The method of claim 6 further characterized in that the wave lengths of said beam of photons are closely centered about a value of 6328 angstroms.

12. The method of claim 6 further characterized in that photons are removed from said stream of photons before it is resolved to form a spectrum, the removed portion consisting of photons at the same frequency as said beam of photons and at a higher frequency than the frequency of said beam of photons.

13. The method of claim 6 further characterized in that composite reference spectra are used in performing said comparison, a composite reference spectrum being prepared for each reference sample by providing a plurality of spectra of each reference sample to the computer and averaging each of said plurality of reference spectra.

14. The method of claim 6 further characterized in that a portion of said Raman spectrum is removed and not provided to the computer, such portion consisting of Rayleigh scattered light and the anti-Stokes lines.

15. The method of claim 6 further characterized in that said unknown spectrum and said reference spectra are adjusted to substantially remove false information before said comparison is accomplished.

16. The method of claim 15 further characterized in that said false information comprises a background spectrum, which is obtained in the same general manner as a sample spectrum but with said beam of photons interrupted, and said adjustment to remove false information is accomplished by subtracting the background spectrum intensity from the sample spectrum intensity at each frequency.

17. The method of claim 15 further characterized in that said false information comprises sample fluorescence and stray photons and said adjustment to remove false information is accomplished by means of establishing baselines and discarding that portion of the spectrum which is below the baselines.

18. Apparatus for determining the composition of an unknown sample comprising:
(a) means for producing a beam of photons which is substantially monochromatic and impinges on the unknown sample;
(b) means for collecting photons scattered by the unknown sample into a stream of scattered photons;
(c) means for resolving the photon stream into its component frequencies to form a Raman spectrum of the unknown sample;
(d) means for converting said unknown sample Raman spectrum to digital form and transmitting said unknown spectrum to computing means;
(e) said computing means, which contain reference spectra obtained in the same manner as said unknown spectrum, where the reference spectra are of reference samples whose composition is known; and,
(f) means within the computing means for identifying substances present in the unknown sample by comparing said unknown spectrum to the reference spectra, said computing means accomplishing said comparison by performing the following functions:
   (i) inspecting the unknown spectrum and selecting a plurality of separate spectral analysis regions;
   (ii) determining a size characteristic associated with each spectral analysis region of the unknown spectrum;
   (iii) searching the reference spectra and choosing those reference spectra having in the selected spectral analysis regions features corresponding to those of the selected spectral analysis regions of the unknown spectrum and size characteristics substantially identical to those of the selected spectral analysis regions of the unknown spectrum;
   (iv) if more than one reference spectrum is chosen, repeating functions (f)(i), (f)(ii), and (f)(iii), selecting additional regions, until only one reference spectrum is chosen, the substances present in said one chosen reference spectrum being present in the unknown sample;
   (v) if no reference spectrum is chosen, establishing a number of working hypothesis, each hypothesis being that the unknown sample consists of a different combination of the reference samples which exhibited the spectra chosen to have features corresponding to those of the selected regions of the unknown spectrum;
   (vi) testing each working hypothesis by combining the spectra of the hypothesis to produce a single hypothetical spectrum and comparing it to the unknown spectrum;
   (vii) discarding each working hypothesis which is not substantially identical to the unknown spectrum; and,
   (viii) if more than one working hypothesis has not been discarded, repeating functions (f)(v) through (f)(viii), selecting additional regions, until only one working hypothesis has not been discarded, the unknown sample composition then being that of said one remaining working hypothesis.

19. The apparatus of claim 18 further characterized with respect to function (f)(vi) in that said testing is accomplished by:
(a) for each working hypothesis, establishing a set of equations consisting of one equation associated with each selected region of the unknown spectrum, which equation describes the area of the region in terms of concentrations of the reference samples and areas of reference spectra regions; and
(b) attempting to solve each set of equations and concluding that each working hypothesis whose set of equations cannot be completely solved or yields unreal numbers is not substantially identical to the unknown spectrum.

20. The apparatus of claim 19 further characterized in that said equation associated with each region is of the form $$X_1C_1 + X_2C_2 + \ldots + X_nC_n = A,$$

Where
- $C_1, C_2, \ldots C_n$ = the concentration of the substance of reference samples 1, 2, ... n in the hypothetical combination of reference samples,
- $X_1, X_2, \ldots X_n$ = the areas of those regions in each of the reference spectra of the hypothetical combination, and
- $A$ = the area of the region of the unknown spectrum.

21. Apparatus for performing a quantitative analysis for preselected substances of an unknown sample comprising:
   (a) means for producing a beam of photons which is substantially monochromatic and impinges on the unknown sample;
   (b) means for collecting photons scattered by the unknown sample into a stream of scattered photons;
   (c) means for resolving the photon stream into its component frequencies to form a Raman spectrum of the unknown sample;
   (d) means for converting said unknown sample Raman spectrum to digital form and transmitting said unknown spectrum to computing means;
   (e) said computer means, which contain reference spectra obtained in the same manner as said unknown spectrum, where the reference spectra are of reference samples whose quantitative composition is known and where each reference sample is comprised of at least one of said preselected substances; and,
   (f) means within the computer for identifying substances present in the unknown sample by comparing said unknown spectrum to the reference spectra, said computer accomplishing said comparison by performing the following functions:
      (i) inspecting the reference spectra and selecting a plurality of separate spectral analysis regions;
      (ii) determining the areas of the selected regions for each reference spectrum and for the unknown spectrum;
      (iii) establishing a relationship between said reference spectra region areas and concentrations of said preselected substances in said reference sample; and
      (iv) determining the concentrations of said preselected substances in said unknown sample by applying the relationship established in function (f)(iii) to the unknown spectrum region areas.

22. The apparatus of claim 21 further characterized with respect to element (f) in that said relationship is established and said concentrations determined by the following functions:
   (a) selecting a number of spectral analysis regions equal to the number of said preselected substances;
   (b) determining the areas of the selected regions for each reference spectrum and for the unknown spectrum and calculating area fractions;
   (c) establishing a set of equations for each reference sample where the number of equations in each set is equal to the number of said preselected substances and each equation describes the concentration of one preselected substance in terms of its contributions to region areas, each equation having the form $$X = C_{1x}A_1 + C_{2x}A_2 + \ldots + C_{nx}A_n,$$

where
- X represents the concentration fractions of the preselected substance,
- $A_1, A_2, \ldots A_n$ are area fractions of the selected regions of the spectrum of the reference sample where n equals the number of regions, and
- $C_{1x}, C_{2x}, \ldots C_{nx}$ are coefficients associated with the contributions of the preselected substances to the regions;

(d) solving all of the equations established in function (c) for said coefficients:
   (e) establishing one set of equations for the unknown sample as was done in function (c) for each reference sample; and,
   (f) solving said unknown sample equations for the concentrations of the preselected substances, using the coefficients determined in function (d).

23. The apparatus of claim 21 further characterized with respect to functions (f)(iii) and (f)(iv) in that said relationship is established and said concentrations determined by:
   (a) expressing said reference sample concentrations in terms of concentration fractions and arranging the concentration fractions in a concentration fraction matrix, according to said reference samples and said preselected substances;
   (b) calculating area fractions from said reference spectra region areas and arranging the area fractions into an area fraction matrix, according to said reference samples and the selected regions;
   (c) determining a transpose matrix, which is the transpose of the area fraction matrix;
   (d) forming a mathematical relationship using said matrices, as follows:

$$\frac{\text{concentration fraction matrix} \times \text{tranpose matrix}}{\text{area fraction matrix} \times \text{tranpose matrix}};$$

(e) solving said mathematical quantity to yield a matrix, which consists of correlation coefficients, arranged according to the selected regions and said preselected substances;
   (f) calculating area fractions from said unknown spectrum region areas and arranging the area fractions in a matrix; and,
   (g) multiplying said correlation coefficients matrix by the matrix formed of said unknown spectrum area fractions to obtain a product which is a concentration fraction matrix which expresses the concentrations of the preselected substances in said unknown sample.

24. The apparatus of claim 21 further characterized in that the substances comprising said unknown sample are paraffins, naphthenes, and aromatics.

25. The apparatus of claim 21 further characterized in that said beam of photons is from a laser source.

26. The apparatus of claim 21 further characterized in that the wave lengths of said beam of photons are closely centered about a value of 6328 angstroms.

27. The apparatus of claim 21 further comprising means for removing photons from said stream of photons before it is resolved to form a spectrum, the removed portion consisting of photons at the same frequency as said beam of photons and at a higher frequency than the frequency of said beam of photons.

28. The apparatus of claim 21 further comprising means for using composite reference spectra in performing said comparison, a composite reference spectrum being prepared for each reference sample by providing a plurality of spectra of each reference sample to said computer means and averaging each of said plurality of reference spectra.

29. The apparatus of claim 21 further comprising means for removing a portion of said Raman spectrum, such portion consisting of Rayleigh scattered light and the anti-Stokes lines.

30. The apparatus of claim 21 further comprising means for adjusting said unknown spectrum and said reference spectra to substantially remove false information before said comparison is accomplished.

31. The apparatus of claim 30 further characterized in that said spectrum adjusting means comprises means for providing to said computer means a background spectrum for use in accomplishing said adjustment to remove false information, said background spectrum being obtained in the same general manner as a sample spectrum but with said beam of photons interrupted, and said adjustment to remove false information being accomplished by subtracting the background spectrum intensity from the sample spectrum intensity at each frequency.

32. The apparatus of claim 30 further comprising means for substantially removing those portions of the spectra which comprise sample fluorescence and stray photons by means of establishing baselines and discarding that portion of the spectrum which is below the baselines.

* * * * *